(12) United States Patent
Trimper et al.

(10) Patent No.: US 8,695,054 B2
(45) Date of Patent: Apr. 8, 2014

(54) INGESTING HETEROGENEOUS VIDEO CONTENT TO PROVIDE A UNIFIED VIDEO PROVISIONING SERVICE

(75) Inventors: John K. Trimper, Groton, MA (US); Arthur C. Claxton, Vienna, VA (US)

(73) Assignees: Verizon Patent and Licensing Inc., Basking Ridge, NJ (US); Verizon Virginia LLC, Ashburn, VA (US)

( * ) Notice: Subject to any disclaimer, the term of this patent is extended or adjusted under 35 U.S.C. 154(b) by 62 days.

(21) Appl. No.: 13/196,727

(22) Filed: Aug. 2, 2011

(65) Prior Publication Data

US 2012/0079527 A1    Mar. 29, 2012

Related U.S. Application Data

(60) Provisional application No. 61/387,939, filed on Sep. 29, 2010.

(51) Int. Cl.
*H04N 7/173* (2011.01)
*H04N 7/16* (2011.01)
*H04N 9/88* (2006.01)

(52) U.S. Cl.
USPC .............. 725/115; 725/93; 725/145; 386/278

(58) Field of Classification Search
USPC ................. 725/91, 82, 114; 386/278
See application file for complete search history.

(56) References Cited

U.S. PATENT DOCUMENTS

| | | | |
|---|---|---|---|
| 7,617,436 B2 * | 11/2009 | Wenger et al. ................ | 714/758 |
| 7,948,949 B2 * | 5/2011 | Bowen .......................... | 370/331 |
| 2004/0001087 A1 * | 1/2004 | Warmus et al. ............... | 345/745 |
| 2004/0015445 A1 * | 1/2004 | Heaven et al. ................ | 705/51 |
| 2006/0195870 A1 * | 8/2006 | Teichner et al. ............... | 725/75 |
| 2006/0218600 A1 * | 9/2006 | Johnson ......................... | 725/87 |
| 2006/0244839 A1 * | 11/2006 | Glatron et al. ........... | 348/211.11 |
| 2007/0196076 A1 * | 8/2007 | Jeong et al. .................... | 386/83 |
| 2007/0220588 A1 * | 9/2007 | Panda et al. ....................... | 726/1 |
| 2008/0189753 A1 * | 8/2008 | Nesvadba et al. ............. | 725/105 |
| 2009/0171966 A1 * | 7/2009 | Heaven et al. ..................... | 707/9 |
| 2009/0300450 A1 * | 12/2009 | Tzannes ........................ | 714/748 |
| 2010/0095181 A1 * | 4/2010 | Ma et al. ....................... | 714/748 |
| 2010/0128649 A1 * | 5/2010 | Gonsa et al. ................... | 370/312 |
| 2010/0146567 A1 * | 6/2010 | Mehta et al. .................... | 725/91 |
| 2010/0332935 A1 * | 12/2010 | Tzannes ........................ | 714/748 |
| 2011/0002331 A1 * | 1/2011 | Tzannes ........................ | 370/389 |
| 2011/0268422 A1 * | 11/2011 | Jeong et al. .................... | 386/241 |
| 2011/0273618 A1 * | 11/2011 | Takahashi et al. ............. | 348/575 |
| 2012/0079523 A1 * | 3/2012 | Trimper et al. ................. | 725/28 |
| 2012/0079527 A1 * | 3/2012 | Trimper et al. ................. | 725/31 |
| 2012/0079528 A1 * | 3/2012 | Trimper et al. ................. | 725/31 |
| 2012/0079606 A1 * | 3/2012 | Evans et al. .................... | 726/28 |
| 2012/0263063 A1 * | 10/2012 | Catrein et al. ................. | 370/252 |

* cited by examiner

*Primary Examiner* — James R Sheleheda

(57) ABSTRACT

A system may receive a video asset from a content provider. The system may process the video asset to allow a video provisioning system to distribute the video asset to a set top box and another device that is a different type of device than the set top box. Processing the video asset may include verifying that the video asset conforms to one or more predetermined formats, decrypting the video asset, verifying that the video asset complies with a particular standard of quality, or transcoding the video asset in a manner that is supported by the set top box and the other device. The system may store the transcoded video asset.

21 Claims, 8 Drawing Sheets

| CONTENT PROVIDER ID 605 | SOURCE 610 |
| CONTENT TYPE 615 | TAXONOMY 620 |
| METADATA TRANSFORM POLICY 625 | DECRYPTION POLICY 630 |

INGESTING HETEROGENEOUS VIDEO CONTENT TO PROVIDE A UNIFIED VIDEO PROVISIONING SERVICE

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND

Users, of user devices, have a growing array of sources, networks, and/or content providers from which to obtain video content and/or services. The users may use video client devices (e.g., a set top box, etc.) to obtain free broadcast television video content (e.g., from Fox, ABC, CBS, etc.), on-demand video content (e.g., Video On-Demand (VOD), pay-per-view (PPV), etc.), and/or pay television video content (e.g., from HBO, Cinemax, etc.) from cable television operators (e.g., Comcast, Time Warner, etc.) and/or satellite television operators (e.g., DirectTV, Dish Network, etc.). The users may use computer devices, wireless mobile handset devices, etc. to obtain other video content from on-line content providers, such as television operators (e.g., ABC, Fox, CBS, etc.), over-the-top (OTT) content providers (e.g., Hulu, Veoh, Jaman, YouTube, etc.), and/or other commercial content providers (e.g., Apple Computer's iTunes, Netflix, Blockbuster, etc.).

BRIEF DESCRIPTION OF THE DRAWINGS

FIG. 6 is a diagram of an example data structure that stores policy information, associated with a content provider, according to an implementation described herein;

DETAILED DESCRIPTION OF PREFERRED EMBODIMENTS

Figure 1:
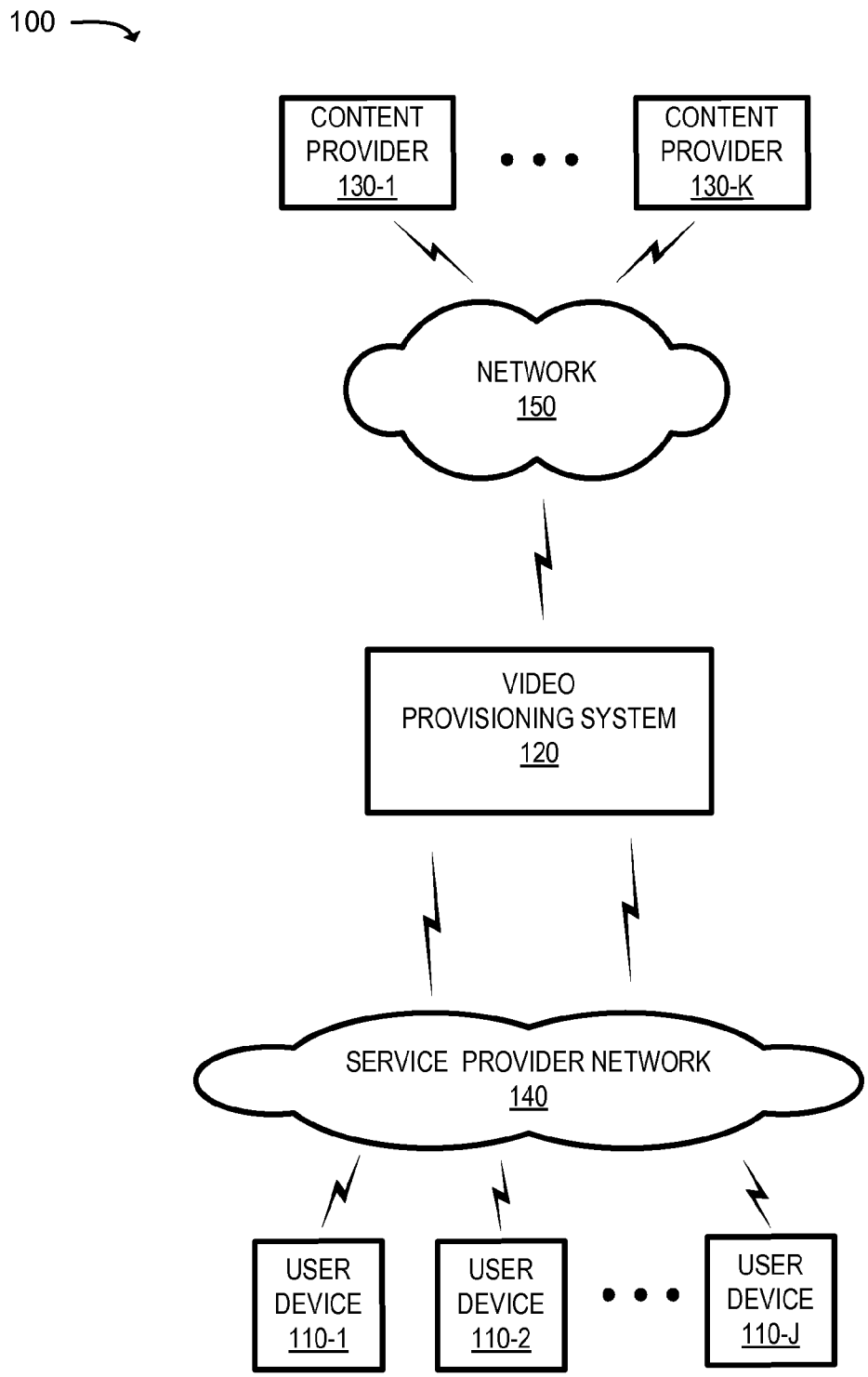
FIG. 1 is a diagram of an example environment in which the systems and/or methods, described herein, may be implemented.

The following detailed description refers to the accompanying drawings. The same reference numbers in different drawings may identify the same or similar elements.

Systems and/or methods, described herein, may enable video content, of different formats, to be acquired by a video content management system (VCMS). The systems and/or methods may enable the VCMS to process the acquired video content to allow a video provisioning system, with which the VCMS is associated, to provide a video provisioning service to different types of user devices. The video provisioning service may enable the video content to be accessed, obtained, and/or played by the different types of user devices.

The different types of user devices may, for example, include computer devices (e.g., desktop computers, laptop computers, and tablet computers), wireless handset devices (e.g., mobile phones, smart phones, personal digital assistants (PDAs), and tablet computers), and/or set top boxes. Additionally, the video content may be provisioned to the various types of user devices via a number of different types of networks, such as, for example, a wired network, a wireless network, a broadband network, a cellular telephone network, a television network, etc., and/or some combination thereof.

The term video content, as used herein, may include one or more video assets, information associated with data rights management (DRM) that corresponds to the video assets, and/or metadata associated with the video assets. The video assets may include Video On-Demand (VOD) video content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. The information associated with the DRM may include license information that identifies terms and/or conditions for handling, promoting, distributing, and/or using the video assets and/or enables video assets to be encrypted and/or decrypted (e.g., based on keys associated with the license information).

The metadata may enable the video assets to be identified, managed, offered, and/or distributed to a user device. The metadata may, for example, include an identifier associated with a video asset (e.g., a number, a name, a title, etc.); a genre of the video asset (e.g., horror, comedy, adult, etc.); a category of the video asset (e.g., VOD asset, a PPV asset, an on-line asset, etc.); a text description of the video asset; and/or information associated with artists associated with the video asset (e.g., names of actors, directors, producers, etc.). The metadata may also, or alternatively, include information identifying a type of the video asset (e.g., a movie, music video, a game, etc.); a rating associated with the video asset (e.g., general audience (G), parental guidance (PG), PG-13, restricted (R), mature audience (MA), etc.); user reviews associated with the video asset; a price associated with the video asset (e.g., a sale price, a rental price per day, a pay-per-view price, etc.); and/or an availability period associated with the video asset (e.g., release dates, restriction periods, blackout periods, etc.). The metadata may also, or alternatively, include information associated with a storage location (e.g., a uniform resource locator (URL)) corresponding to the video asset; a format associated with the video asset (e.g., a resolution level, compression/decompression (CODEC) information, a screen size, a frame size, a frame refresh rate, a bit rate, etc.); and/or types of user devices supported by each format, etc.

FIG. 1 is a diagram of an example environment in which the systems and/or methods, described herein, may be implemented. As shown in FIG. 1, environment 100 may include a group of user devices 110-1, . . . , 110-J (where J≥1) (hereinafter referred to collectively as "user devices 110" and individually as "user device 110"), a video provisioning system (VPS) 120, a group of content providers 130-1, . . . , 130-K (where K≥1) (hereinafter referred to collectively as "content providers 130" and individually as "content provider 130"), a service provider network 140, and a network 150. The number of devices, systems, and/or networks, illustrated in FIG. 1, is provided for explanatory purposes only. In practice, there may be additional devices, systems, and/or networks; fewer devices, systems, and/or networks; different devices, systems, and/or networks; or differently arranged devices, systems, and/or networks than illustrated in FIG. 1.

Also, in some implementations, one or more of the devices of environment 100 may perform one or more functions described as being performed by another one or more of the devices of environment 100. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, or another type of computation or communication device.

User device 110 may communicate with VPS 120 and/or perform certain operations to obtain a video asset from VPS 120. For example, user device 110 may access a portal (e.g., a website, a user interface, an interactive program guide, etc.) associated with VPS 120, to browse, search, select, and/or obtain a video asset. User device 110 may obtain information associated with DRM, with respect to the video asset, and may use license information, obtained from the information associated with the DRM, to decrypt the video asset for playing on user device 110.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. VPS 120 may communicate with one or more content providers 130 to acquire video content. VPS 120 may connect to a collection of various types user devices 110 associated with a user, such as, for example, a set top box, a computer device, a wireless handset device (e.g., a smart phone, a personal digital assistant (PDA), etc.), and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video content to be offered and/or distributed to the different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., VOD, PPV, etc.). A media stream, as used herein, may refer to a stream of content that includes video content (e.g., a video stream), audio content (e.g., an audio stream), and/or textual content (e.g., a textual stream).

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Figure 2:
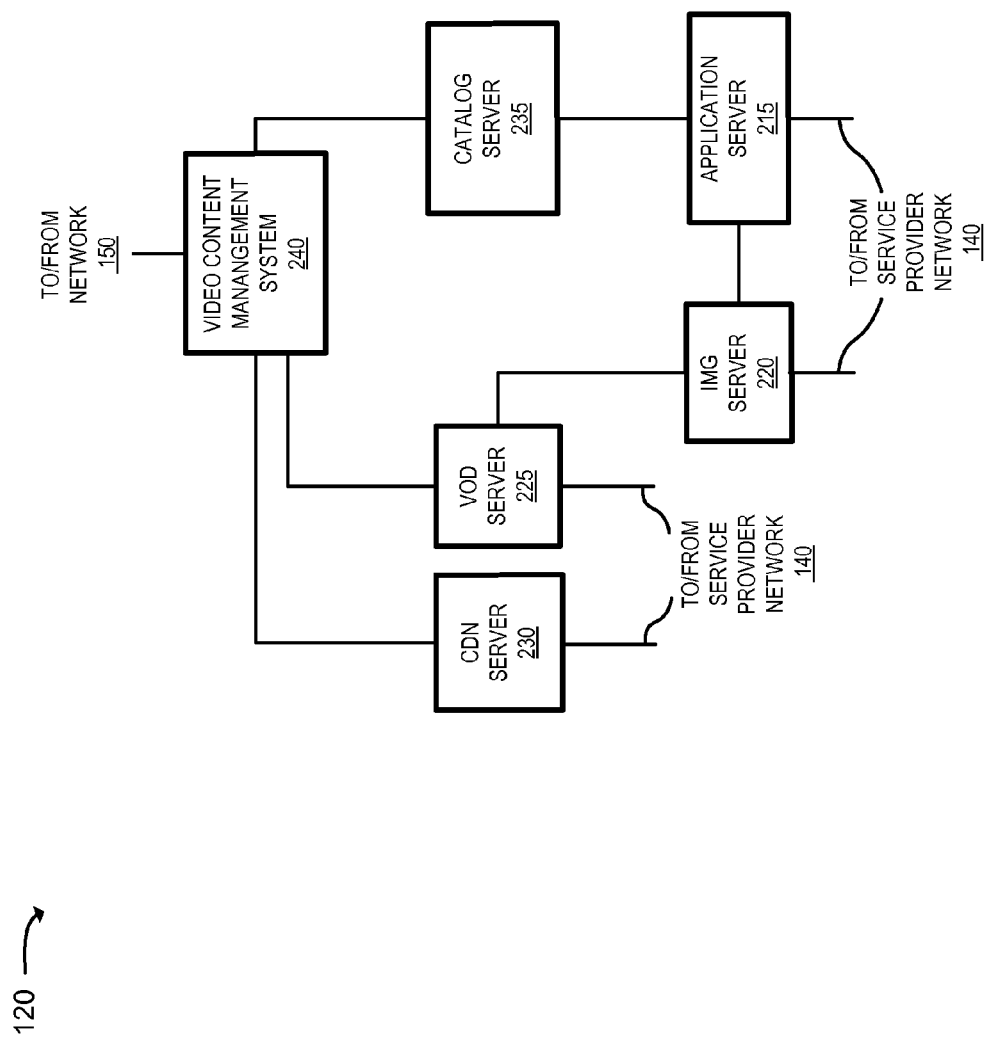
FIG. 2 is a diagram of example devices, associated with the video provisioning system, of FIG. 1.

FIG. 2 is a diagram of example devices associated with VPS 120. VPS 120 may include an application server 215, an interactive media guide (IMG) server 220, a video on-demand (VOD) server 225, a content delivery network (CDN) server 230, a Catalog server 235, and a video content management (VCM) system 240. Although FIG. 2 shows example devices of VPS 120, in other implementations, VPS 120 may include fewer devices, additional devices, different devices, or differently arranged devices than depicted in FIG. 2. Additionally, or alternatively, one or more devices of VPS 120 may perform one or more tasks described as being performed by one or more other devices of VPS 120.

In the description below, VOD server 225 is described as provisioning video services for a type of user device 110 (i.e., a set top box) and CDN server 230 is described as provisioning video services for another other type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing a store front portal (i.e., via an IMG), that can be accessed by the set top box, and application server 215 is described as providing another store front portal (e.g., via a web page, a user interface, an interactive program guide, etc.), that can be accessed by the other types of user devices 110, for explanatory purposes. In another implementation, the store front portal may be provisioned for the set top box and/or the other types of user devices 110 in a number of ways. For example, IMG server 220 and/or application server 215 may be combined into a single device that provisions the store front portal for each type of user device 110. In another example, the store front portal may be provisioned, for each type of user device 110, by another device and/or network instead of, or in combination with, IMG server 220 and/or application server 215. Thus, the examples below are provided for explanatory purposes only.

Application server 215 may include one or more server devices, or other types of computation or communication devices, that gather, process, search, store, and/or provide information in a manner similar to that described herein. Application server 215 may receive metadata that has been published by Catalog server 235. The metadata may be associated with video assets that are to be made available and/or offered (e.g., for sale, rent, subscription, etc.) to user devices 110. Application server 215 may host a portal (e.g., a VPS store front), such as a private website (e.g., for subscribing user devices 110), a public website (e.g., for non-subscribing user devices 110), a user interface (UI) (e.g., that is accessible by wireless handset user devices 110, etc.), an interactive program guide (e.g., an IMG for set top box-type user devices 110) and/or other types of user interfaces. The portal may enable single sign-on (SSO) portal access, to a user of one or more user devices 110, based on the same login credentials (e.g., username, password, personal identification number (PIN), etc.). Application server 215 may publish all or a portion of the metadata to the portal that permits any of user devices 110 to browse, perform searches, process payment, etc. for video assets based on the metadata that is published to the portal.

IMG server 220 may include one or more server devices, or other types of computation or communication devices, that gather, process, search, store, and/or provide information in a manner similar to that described herein. IMG server 220 may, for example, process metadata, that has been published by Catalog server 235 and/or VOD server 225, in a manner similar to that described above (e.g., with respect to application server 215). The metadata may be associated with video content that may be obtained by a particular type of user device 110, such as a set top box user device 110.

IMG server 220 may publish all or a portion of the metadata to an IMG user interface (UI) that the set top box user device 110, associated with the user, may render for display on a video display device. IMG server 220 may permit the set top box user device 110 to access information associated with video assets, stored by VOD server 225, and access the actual video assets. IMG server 220 may, in another example implementation, communicate with application server 215, which may permit the set top box user device 110 to access the metadata associated video assets that are stored in CDN server 230.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM system 240. VOD server 225 may store the published video assets in a memory associated with VOD server 225. VOD server 225 may publish a portion of the metadata, associated with video assets (e.g., that are available for release and/or not subject to a blackout, etc.), to IMG server 220.

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 110. CDN server 230 may actually represent a content delivery network that includes multiple routing and/or storage devices.

CDN server 230 may receive published video assets in multiple video formats from VCM system 240. CDN server 230 may store the published video assets in a memory associated with CDN server 230. CDN server 230 may identify a respective storage location and/or URL for each format of each video asset that are stored within the memory and may send information associated with the storage locations and/or the URLs to Catalog server 235.

Catalog server 235 may include one or more server devices, or other types of computation or communication devices, that gather, process, search, store, and/or provide information in a manner similar to that described herein. Catalog server 235 may, for example, receive, from VCM system 240, published metadata associated with video assets that have been published to VOD server 225 and/or CDN server 230. Catalog server 235 may identify, from the metadata, information associated with the availability of the video assets based on dates on which the video assets are released, blacked out, etc. Catalog server 235 may process and/or package the metadata in order to offer, to user devices 110, the video assets to which the metadata corresponds. The processed metadata, associated with the video assets, may include identifiers (e.g., video asset numbers, titles, etc.), prices (e.g., sale prices, rental prices, subscription prices, etc.), descriptions (e.g., a synopsis, a summary, etc. of the video assets), ratings, reviews, genres, casting information (e.g., actors, directors, producers, etc.), etc. Catalog server 235 may, for example, publish the metadata to the store front portal associated with VPS application 215. Catalog server 235 may not publish metadata associated with video assets that are identified as not yet being available.

VCM system 240 may include one or more server devices, or other types of computation or communication devices, that gather, process, search, store, and/or provide information in a manner similar to that described herein. VCM system 240 may, for example, communicate with content providers 130 to acquire high quality video content (e.g., video content that includes video assets associated with the resolution level and/or bit rate that is greater than a threshold) from content providers 130. VCM system 240 may perform an operation, on the acquired video content, that allows the video content to be ingested by VCM system 240. VCM system 240 may process the ingested video content so that the ingested video content is supported by different types of user devices 110 (e.g., set top boxes, computer devices, handheld wireless devices, gaming devices, etc.). Additionally, VCM system 240 may publish the ingested video content to one or more devices, associated with VPS 120, that allows the published video content to be offered and/or distributed to the different types of user devices 110 by VPS 120.

Figure 3:
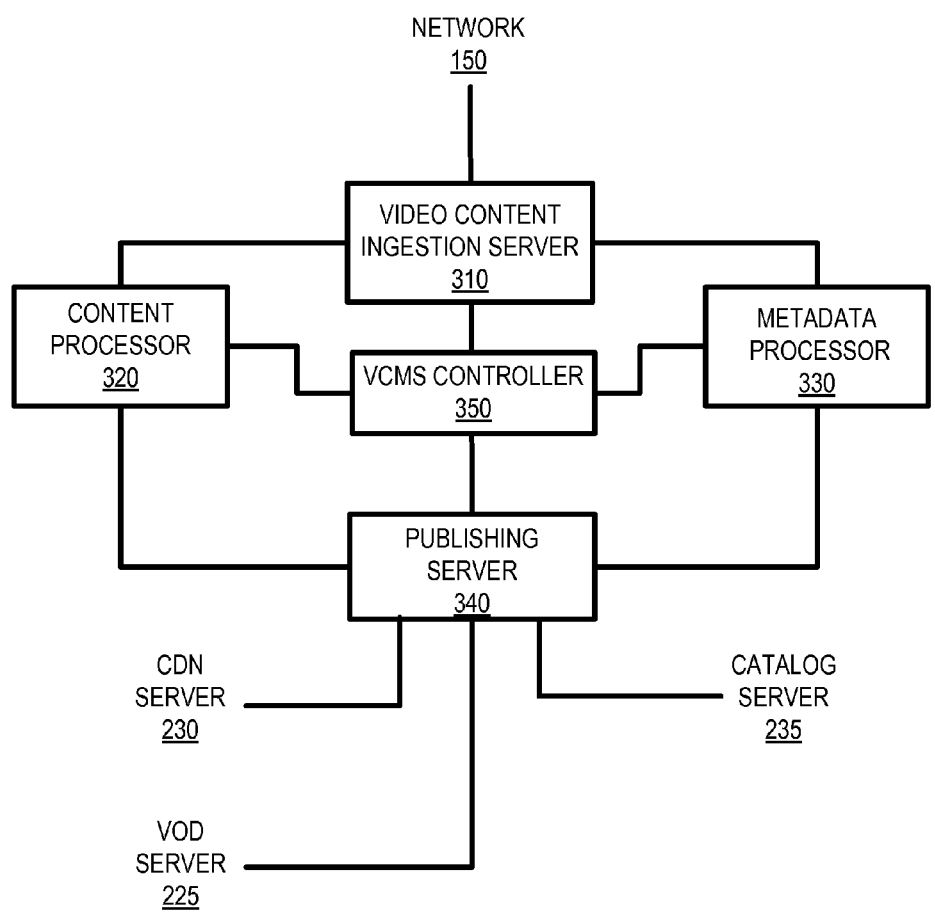
FIG. 3 is a diagram of example devices, associated with a video content management system, of FIG. 2.

FIG. 3 is a diagram of example devices associated with VCM system 240. VCM system 240 may include a video content ingestion server 310 (hereinafter referred to as "ingestion server 310"), a content processor 320, a metadata processor 330, a publishing server 340, and a video content management system (VCMS) controller 350. Although FIG. 3 shows example devices of VCM system 240, in other implementations, VCM system 240 may include fewer devices, additional devices, different devices, or differently arranged devices than depicted in FIG. 3. For example, some or all of the devices, associated with VCM system 240 could be combined into a single device. Additionally, or alternatively, one or more devices of VCM system 240 may perform one or more tasks described as being performed by one or more other devices of VCM system 240.

Ingestion server 310 may include one or more server devices, or other types of computation or communication devices, that gather, process, search, store, and/or provide information in a manner similar to that described herein. Ingestion server 310 may, for example, perform operations associated with acquiring and/or ingesting video content, for use by VPS 120, to provide a video provisioning service to the different types of user devices 110.

Ingestion server 310 may, for example, communicate with content provider 130, via network 150, to acquire the video content (e.g., using a file transfer protocol (FTP) and/or some other protocol) and may temporarily store the acquired video content in a memory associated with VCM system 240 (e.g., sometimes referred to as an "ingest memory"). In another example, ingestion server 310 may monitor another memory that is accessible by content provider 130 and/or that temporarily stores video content that is downloaded, to the other memory, by content provider 130. Ingestion server 130 may detect video content, within the other memory, and may store a copy of the video content in the ingest memory. In yet another example, ingestion server 310 may acquire video content by reading video content from a portable storage device, such as a video tape, a digital versatile disc (DVD), a memory card, etc., and may temporarily store the acquired video content in the ingest memory. In still another example, ingestion server 310 may acquire the video content via a media stream (e.g., a video stream that includes on-air video content and/or other video content) received from content provider 130 and may temporarily store the acquired video content in the ingest memory. Ingestion server 310 may also acquire video content from content provider 130 via a remote server device (e.g., a web server), associated with network 150, and may store the acquired video content in the ingest memory.

Ingestion server 310 may verify the content, of the acquired video content, to ensure that the video content is in a particular format and/or is complete when acquired from content provider 130. Ingestion server 310 may retrieve, from another memory associated with VCM system 240, policy information associated with content provider 130 and may use the policy information to determine whether the acquired video content is complete and/or is in the particular format.

Ingestion server 310 may obtain high quality video assets, from the acquired video content, and may initiate an operation to ingest the video assets into VPS 120. The high quality video assets may be associated with a level of resolution that is greater than a threshold or a bit rate that is greater than another threshold. In another example, ingestion server 130 may, based on the policy information, decrypt the video assets to allow further processing to be performed on the video assets and/or to temporarily store the decrypted video assets in the ingest memory.

Ingestion server 310 may obtain metadata, associated with the video assets, from the acquired video content and/or may decrypt the metadata. Ingestion server 310 may, in another example, convert the metadata into a format and/or file type that can be processed by ingestion server 310. Ingestion server 310 may temporarily store the metadata in the ingest memory and/or another memory (sometimes referred to as a "metadata repository").

Content processor 320 may include one or more devices, or other types of computation or communication devices, that gather, process, search, store, and/or provide information in a manner similar to that described herein. Content processor 320 may process video assets received from ingestion server 310.

Content processor 320 may, for example, perform a quality control and/or quality analysis operation on decrypted video assets received from ingest server 310 and/or retrieved from the ingest memory. For example, content processor 320 may analyze each of the video assets to identify a condition (e.g., a gap within a video signal, a distorted video signal, etc.) within the video asset. The condition may, for example, correspond to a portion and/or gap, within the video asset, where there is no video signal and/or that renders a blank screen when displayed via user device 110. Content processor 320 may reduce a size and/or time period associated with the gap. In another example, content processor 320 may check each of the video assets to determine whether the video assets comply with video and/or audio standards (e.g., Moving Picture Experts Group (MPEG)-2, MPEG-4, International Telecommunication Union (ITU) Video Coding Experts Group (VCEG) H.264, Video Coding (VC)-1, etc.), formats (e.g., quarter common intermediate format (QCIF), CIF, standard definition (SD), high definition (HD), etc.), and/or specifications that are utilized by VPS 120 and/or specified by an operator associated with VPS 120.

Content processor 320 may perform an operation to repair and/or reformat a video asset that does not comply with the video and/or audio standards, formats, and/or specifications. Content processor 320 may, in another example, receive instructions from an operator of VCM system 240 and may execute the instructions to repair and/or reformat the video asset. Content processor 320 may send a request to content provider 130 to reacquire video content, with which the video asset is associated, based on a determination that the video asset that content processor 320 is not able to repair and/or reformat the video asset.

Content processor 320 may store the video asset in a memory associated with VCM system 240 (sometimes referred to as a "mezzanine memory"). The video asset, stored in the mezzanine memory, may be used as a source video asset from which copies may be generated for other processing and/or formatting, as part of a recovery process (e.g., to restore video assets that may have been lost, etc.), and/or for other purposes. In one example, content processor 320 may use the source video asset to generate copies of the video asset.

Content processor 320 may process and/or transcode the copies of the video assets into formats that can be supported (e.g., received, processed, played, etc.) by different types of user devices 110 (e.g., set top boxes, computer devices, wireless mobile handsets, gaming devices, etc.). For example, each copy may correspond to respective different formats associated with unique bit rates, levels of resolution (e.g., standard definition, high definition, etc.), frame refresh rates, screen sizes (e.g., aspect ratios, dimensions, etc.), compression/decompression (CODEC) ratios, etc. that can be supported by wireless handset devices, computer devices, set top boxes, gaming devices, etc. Content processor 320 may store the transcoded copies of the video assets in another memory associated with VCM system 240 (sometimes referred to as a "publish memory"). Storing the transcoded copies of the video asset in the publish memory may allow publishing server 340 to perform a publication operation on the transcoded copies of the video assets in order for VPS 120 to offer and/or distribute the video assets to the different types of user devices 110.

Metadata processor 330 may include one or more devices, or other types of computation or communication devices, that gather, process, search, store, and/or provide information in a manner similar to that described herein. Metadata processor 330 may process metadata received from ingestion server 310.

Metadata processor 330 may perform a quality control operation on metadata received from ingestion server 310 and/or retrieved from the ingest memory. For example, metadata server 330 may check the metadata to determine whether the images, text, and/or other types of metadata comply with metadata standards (e.g., image standards, image types, data standards, etc.) and/or specifications that are utilized by VPS 120 and/or specified by an operator associated with VPS 120.

Metadata processor 330 may perform an operation to repair and/or reformat metadata that does not comply with the metadata standards and/or specifications. Metadata processor 330 may send a request to content provider 130 to reacquire video content based on a determination that the metadata, associated with the acquired video content, does not comply with the metadata standards and/or specification, and/or that metadata processor 330 is not able to repair and/or reformat the metadata. Metadata processor 330 may temporarily store the metadata in the working memory. Temporarily storing the metadata in the working memory enables further processing to be performed on the metadata, such as formatting the metadata in a manner that can be accessed and/or utilized by different types of user devices 110.

Publishing server 340 may include one or more devices, or other types of computation or communication devices, that gather, process, search, store, and/or provide information in a manner similar to that described herein. Publishing server 340 may receive processed video assets from content processor 320 and/or may retrieve the video assets from the working memory. Publishing server 340 may publish the video assets by transmitting the video assets to CDN server 230 and/or VOD server 225. Publishing the video assets to CDN server 230 and/or VOD server 225 may permit different types of user devices 110 (e.g., set top boxes, computer devices, wireless handset devices, gaming devices, etc.) to obtain the video assets and/or to play the obtained video assets.

Publishing server 340 may receive processed metadata from metadata processor 330 and/or may retrieve the metadata from the working memory. Publishing server 340 may publish the metadata by transmitting the metadata to Catalog server 235. Publishing the metadata to Catalog server 235 may permit Catalog server 235 to offer the video assets to the different types of user devices 110 via a store front portal (e.g., a web site, an interactive program guide, a user interface, etc.) that is hosted by application server 215. In another example, publishing server 340 may publish the metadata by transmitting the metadata to VOD server 225, which may be accessible by set top box user devices 110 via another store front portal (e.g., an IMG) hosted by IMG server 220.

VCMS controller 350 may include one or more devices, or other types of computation or communication devices, that gather, process, search, store, and/or provide information in a manner similar to that described herein. VCMS controller 350 may be capable of communicating with ingestion server 310, content processor 320, metadata processor 330, and/or publishing server 340. VCMS controller 350 may, for example, store logic that controls a workflow associated with acquiring, ingesting, processing, and/or publishing video content to be used by VPS 120 to provide a video provisioning service to different types of user devices 110. VCMS may execute the workflow and send instructions to each device, associated with VCM system 240, while VCM system 240 is handling the video content.

VCMS controller 350 may, for example, send an instruction to ingestion server 310 that causes video content to be acquired from content provider 130. VCMS controller 350 may send instructions to content processor 320 and/or metadata processor 330 to ingest and/or process the acquired video content. VCMS controller 350 may send an instruction to publishing server 340 to publish the ingested and/or processed video content to one or more devices associated with VPS 120 for distribution to one or more types of user devices 110.

Figure 4:
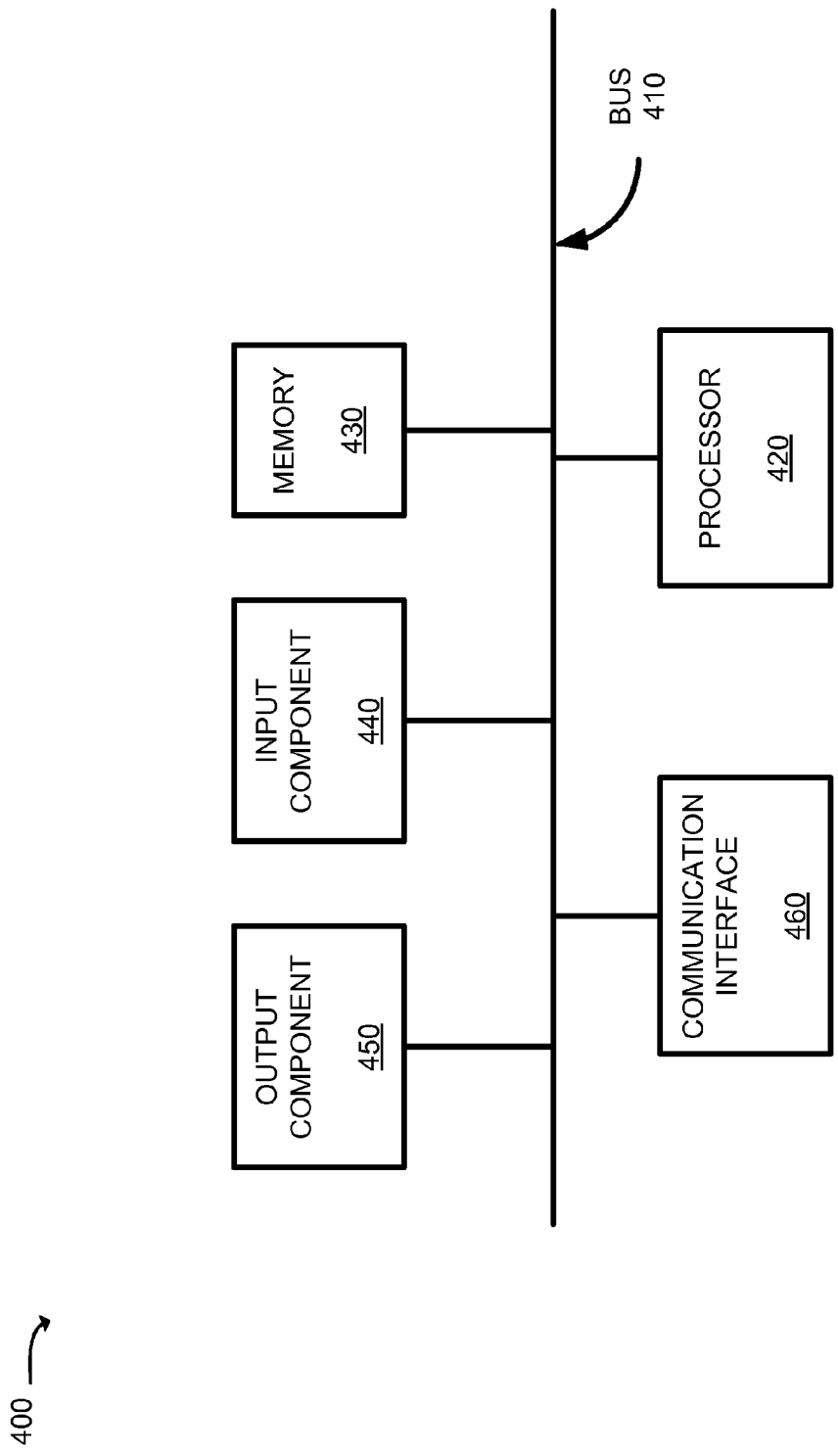
FIG. 4 is a diagram of example components that correspond to one or more of the devices of FIGS. 2 and/or 3.

FIG. 4 is a diagram of example components of a device 400 that may correspond to user device 110, content provider 130, application server 215, IMG server 220, VOD server 225, CDN server 230, Catalog server 235, VCM system 240, ingestion server 310, content processor 320, metadata processor 330, publishing server 340, and/or VCMS controller 350. Alternatively, each of user device 110, content provider 130, application server 215, IMG server 220, VOD server 225, CDN server 230, Catalog server 235, VCM system 240, ingestion server 310, content processor 320, metadata processor 330, publishing server 340, and/or VCMS controller 350 may include one or more devices 400. Device 400 may include a bus 410, a processor 420, a memory 430, an input component 440, an output component 450, and a communication interface 460. Although FIG. 4 shows example components of device 400, in other implementations, device 400 may contain fewer components, additional components, different components, or differently arranged components than depicted in FIG. 4. For example, device 400 may include one or more switch fabrics instead of, or in addition to, bus 410. Additionally, or alternatively, one or more components of device 400 may perform one or more tasks described as being performed by one or more other components of device 400.

Bus 410 may include a path that permits communication among the components of device 400. Processor 420 may include a processor, microprocessor, or processing logic that may interpret and execute instructions. Memory 430 may include any type of dynamic storage device that may store information and instructions, for execution by processor 420, and/or any type of non-volatile storage device that may store information for use by processor 420.

Input component 440 may include a mechanism that permits a user to input information to device 400, such as a keyboard, a keypad, a button, a switch, etc. Output component 450 may include a mechanism that outputs information to the user, such as a display, a speaker, one or more light emitting diodes (LEDs), etc. Communication interface 460 may include any transceiver-like mechanism that enables device 400 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 460 may include mechanisms for communicating with another device or system via a network, such as service provider network 140 and/or network 150. In one alternative implementation, communication interface 460 may be a logical component that includes input and output ports, input and output systems, and/or other input and output components that facilitate the transmission of data to other devices.

As will be described in detail below, device 400 may perform certain operations relating to video content ingestion. Device 400 may perform these operations in response to processor 420 executing software instructions contained in a computer-readable medium, such as memory 430. A computer-readable medium may be defined as a non-transitory memory device. A memory device may include space within a single physical memory device or spread across multiple physical memory devices. The software instructions may be read into memory 430 from another computer-readable medium or from another device. The software instructions contained in memory 430 may cause processor 420 to perform processes described herein. Alternatively, hardwired circuitry may be used in place of or in combination with software instructions to implement processes described herein. Thus, implementations described herein are not limited to any specific combination of hardware circuitry and software.

Figure 5:
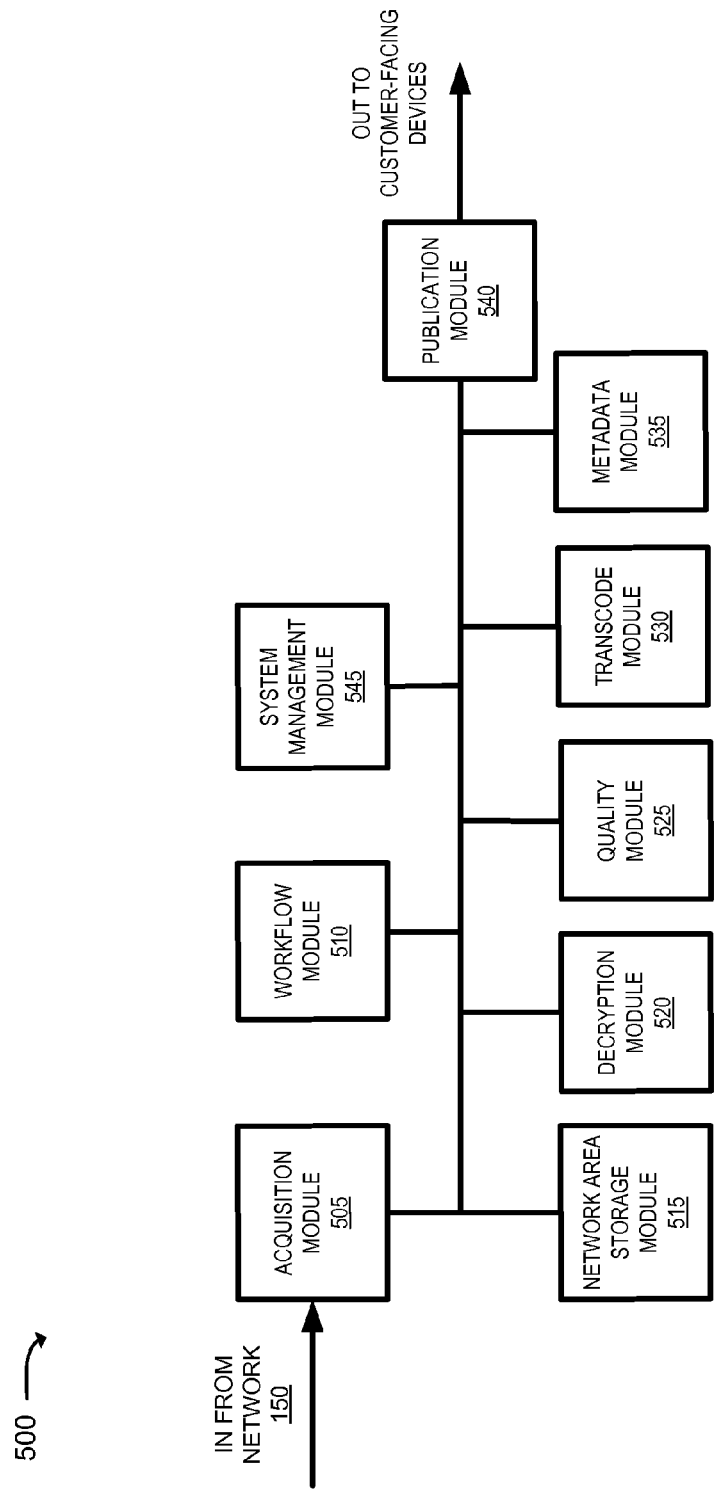
FIG. 5 is a diagram of example functional components that correspond to one or more components of the video content management system of FIG. 2.

FIG. 5 is a diagram of example functional components 500 that correspond to one or more devices of VCM system 240. As shown in FIG. 5, components 500 may include a collection of functional components, such as an acquisition module 505, a workflow module 510, a network area storage (NAS) module 515, a decryption module 520, a quality module 525, a transcode module 530, a metadata module 535, a publication module 540, and a system management module 545. Although FIG. 5 shows example functional components of components 500, in other implementations, components 500 may contain fewer functional components, additional functional components, different functional components, or differently arranged functional components than depicted in FIG. 5. For example, one or more modules may be combined into a single module. Additionally, or alternatively, one or more functional components of components 500 may perform one or more tasks described as being performed by one or more other functional components of components 500.

In the description below, each module, of components 500, is described as being hosted by one or more devices associated with VCM system 240 for explanatory purposes. In another implementation, each of the modules may be hosted by any of the devices associated with VCM system 240 and/or one or more other devices separate from, or in combination with, the devices associated with VCM system 240.

Acquisition module 505 may by hosted by ingestion server 310 and may include logic, implemented using hardware and/or a combination of hardware and software, that enables ingestion server 310 to acquire video content, from content provider 130. Acquisition module 505 may communicate with workflow module 510 to receive instructions and/or to send notifications associated with acquiring and/or processing the video content.

Acquisition module 505 may, for example, receive an instruction, from workflow module 510, to acquire video content from content provider 130. Acquisition module 505 may, in response to the instruction, cause ingestion server 310 to acquire the video content in a manner similar to that described above in FIG. 3. Acquisition module 505 may send a notification to workflow module 510 indicating that video content has been acquired. Acquisition module 505 may cause ingestion server 310 to analyze the video content to verify whether the video content conforms to a particular format and/or that all of the video content has been received in a manner similar to that described above in FIG. 3. Acquisition module 505 may send a notification, to workflow module 510, that that indicates whether the video content conforms to the particular format and/or whether all of the video content (e.g., video files, metadata, DRM information, etc.) has been received.

Workflow module 510 may be hosted by VCMS controller 350 and may include workflow logic, implemented as hardware and/or a combination of hardware and software, that enables VCMS controller 350 to manage the manner in which video content is acquired, ingested, processed, and/or published by VCM system 240. The workflow logic may be predetermined by VCM system 240 and/or may be programmed by an operator of VCM system 240. Workflow module 510 may include one or more application programming interfaces (APIs) that enable workflow module 510 to communicate with each of the function components of functional components 500.

In an example implementation, workflow module 510 and/or the APIs may enable components 500 to act as a service-oriented architecture (SOA). The SOA may permit each function and/or operation, associated with acquiring, ingesting, processing, and/or publishing the video content, to be instantiated, discovered, and/or used, by workflow module 510, as a service based on a time and/or in a manner determined by the workflow logic.

Workflow module 510 may, for example, include an acquisition API that enables workflow module 510 to communicate with acquisition module 505 regarding acquiring and/or ingesting video content. In another example, workflow module 510 may include a NAS storage API that enables workflow module 510 to communicate with NAS storage module 515 regarding storage and/or retrieval of video content while being acquired, ingested, processed, published, etc. Workflow module 510 may include a decryption API that enables workflow module 510 to communicate with decryption module 520 regarding decrypting video assets associated with acquired and/or ingested video content. Workflow module 510 may include a quality API that enables workflow module 510 to communicate with quality module 525 regarding performing a quality operation on ingested video assets and/or metadata associated with the ingested video assets. Workflow module 510 may include a transcode API that enables workflow module 510 to communicate with transcode module 530 regarding transcoding ingested video assets. Workflow module 510 may include a metadata API that enables workflow module 510 to communicate with metadata module 535 regarding ingesting and/or processing metadata associated with the video assets. Workflow module 510 may include a publication API that enables workflow module 510 to communicate with publication module 540 regarding publishing video assets and/or metadata associated with ingested video content. Workflow module 510 may include a system API that enables workflow module 510 to communicate with system management module 545 regarding VCM system 240 performance monitoring and/or control.

Workflow module 510 may receive a notification from one or more modules, of components 500, that identifies a stage, within a process, that a video asset and/or metadata is being acquired, ingested, processed, published, etc. by one or more devices of VCM system 240. Workflow module 510 may, based on the workflow logic, send an instruction that identifies a next step, within the process, to be taken to process the video asset and/or the metadata.

For example, workflow 510 may receive a notification, from acquisition module 505 and via the acquisition API, that indicates that video content has been acquired and/or has been analyzed by ingestion server 310. Workflow module 510 may, in response to the notification, send an instruction to decryption module 520, via the decryption API, that indicates that the acquired video content is to be decrypted. Workflow module 510 may send, via the NAS API, an instruction to NAS module 515 for the decrypted video assets to be temporarily stored in one or more memories (e.g., an ingest memory, etc.) associated with VCM system 240.

Workflow module 510 may send instructions to other functional components to perform processing on video content. For example, workflow module 510 may receive, from decryption module 520 and via the decryption API, an indication that video assets, obtained from ingested video content, have been decrypted. Workflow module 510 may send, via the quality API, an instruction for quality module 525 to perform a quality control operation on the decrypted video assets and/or metadata associated with the decrypted video assets. In another example, workflow module 510 may send, to metadata module 530, an instruction to convert metadata to a format that can be processed by VCM system 240 and/or VPS 120. In yet another example, workflow module 510 may send, to publication module 535 and via publishing API, an instruction for the video assets to be published to customer facing devices (e.g., VOD server 225, CDN server 230, etc.) and/or for the metadata to be published to Catalog server 235 and/or VOD server 225.

NAS module 515 may include logic that enables metadata and/or video assets to be stored and/or retrieved from one or more memories, associated with VCM system 240, depending on which stage the video assets and/or metadata are being processed by VCM system 240. For example, NAS module 515 may enable video content, received from content provider 130, to be temporarily stored in an ingest memory associated with VCM system 240. NAS module 515 may enable video content to be retrieved from the ingest memory that allows operations (e.g., analysis, decryption, quality control, etc.) to be performed to acquire and/or ingest the video content.

NAS module 515 may, in another example, enable ingested video assets (e.g., that have been decrypted, verified for quality, etc.), as source video assets, to be stored in and/or retrieved from a mezzanine memory associated with VCM system 240. NAS module 515 may, in yet another example, enable copies of the source video assets to be stored in and/or retrieved from yet another memory (sometimes referred to as a "publish memory"). The copies of the source video assets may be associated with different formats that are supported by different types of user devices 110 (e.g., a set top box, computer device, wireless handset device, gaming device, etc.). NAS module 515 may, in another example, enable acquired and/or ingested metadata (e.g., that have been decrypted, verified for quality, etc.) to be stored in and/or retrieved from a metadata repository associated with VCM system 240.

Decryption module 520 may by hosted by ingestion server 310 and/or content processor 320 and may include logic, implemented using hardware and/or a combination of hardware and software, that enables acquired video content to be decrypted. Decryption module 520 may communicate with workflow module 510 to receive instructions and/or to send notifications associated with decrypting the acquired video content.

Decryption module 520 may obtain policy information associated with content provider 130 from which video content was received. Decryption module 520 may obtain, from the policy information, information that identifies a manner in which the video assets and/or metadata are to be decrypted. Decryption module 520 may use the policy information to decrypt the video assets and/or the metadata in a manner similar to that described above in FIG. 3.

Quality module 525 may by hosted by ingestion server 310 and/or content processor 320 and may include logic, implemented using hardware and/or a combination of hardware and software, that enables acquired video content (e.g., video content that has been decrypted and/or has verified content and/or formats) to be processed for quality control purposes. Quality module 525 may communicate with workflow module 510 to receive instructions and/or to send notifications associated with processing the acquired video content for quality control.

Quality module 525 may permit the video assets to be verified for quality and/or ingested into VCM system 240 in a manner similar to that described above in FIG. 3.

Transcode module 530 may by hosted by content processor 320 and may include logic, implemented using hardware and/or a combination of hardware and software, that enables copies of ingested video assets to be generated and/or formatted in a manner that can be supported by different types of user devices 110 (e.g., a set top box, a computer device, a wireless handset device, a gaming device, etc.). Transcode module 530 may communicate with workflow module 510 to receive instructions and/or to send notifications associated with transcoding the ingested video assets.

Metadata module 535 may by hosted by metadata processor 330 and may include logic, implemented using hardware and/or a combination of hardware and software, that enables metadata, obtained from the video content, to be acquired and/or processed. Metadata module 535 may communicate with workflow module 510 to receive instructions and/or to send notifications associated with processing the metadata.

Metadata module 535 may enable metadata to be converted into a format that can be processed by VCM system 240 and/or VPS 120. In another example, metadata module 530 may communicate with quality module 525 to enable a quality control processing to be performed on the metadata in a manner similar to that described above.

Publication module 540 may by hosted by publication server 340 and may include logic, implemented using hardware and/or a combination of hardware and software, that enables copies of the video assets to be published by sending the copies of the video assets to customer-facing devices, such as VOD server 225 and/or CDN server 230. Additionally, or alternatively, publication module 540 may enable metadata, associated with the copies of the video assets (e.g., associated with one or more transcoded formats), to be published by sending the metadata to catalogue server 235 and/or VOD server 225.

System management module 545 may by hosted by VCMS controller 350 and may include logic, implemented using hardware and/or a combination of hardware and software, that enables a condition, associated with VCM system 240, to be detected and/or remedied. For example, system management module 545 may communicate with and/or monitor operations associated with one or more devices associated with VCM system 240. System management module 545 may enable an operation to be performed that determines whether a condition, associated with a device within VCM system 240, exists based on communicating with and/or monitoring the operations associated with the devices associated with VCM system 240. System management module 545 may send a notification, to workflow module 510, that identifies whether a condition was detected. The notification may allow workflow module 510 to modify the workflow logic in a manner that enables the video content to be ingested and/or processed and/or a service disruption to be avoided.

FIG. 6 is a diagram of an example data structure 600 that stores policy information, associated with content provider 130, according to an implementation described herein. VCM system 240 may communicate with content provider 130 to obtain policy information associated with video content acquired from content provider 130. In another example, the policy information may be specified by an operator of VCM system 240 based on a service level agreement (SLA) associated with content provider 130. Data structure 600 may include a collection of fields, such as a content provider identifier (ID) field 605, a source field 610, a content type field 615, a taxonomy filed 620, a metadata transform policy field 625, and a decryption policy field 630. Data structure 600 includes fields 605-630 for explanatory purposes. In practice, data structure 600 may include additional fields, fewer fields, different fields, or differently arranged fields than are described with respect to data structure 600.

Content provider identifier (ID) field 605 may store information associated with a particular content provider 130 (e.g., an identifier, a network address, etc.) from which video content is acquired. Source field 610 may store information associated with a storage location at which video content, transmitted by the particular content provider 130, is temporarily stored. For example, the information associated with the storage location may indicate a location within a memory associated with ingestion server 310 at which the video content is temporarily stored (e.g., prior to being acquired and/or ingested by VCM system 240). In another example, the information associated with the storage location may include a URL, associated with a web server (e.g., within network 150) that temporarily stores the video content.

Content type field 615 may store information associated with one or more types of video content that are permitted to be included in the video content received from the particular content provider 130. For example, the information associated with the types of video content may include a type associated with a video asset (e.g., a video files, an audio files, streaming video, streaming audio, control signal files, etc.), another type corresponding to metadata associated with the video asset (e.g., text, image, data, etc.), a further type associated with information associated with DRM (e.g., a key, a license, etc.).

Taxonomy field 620 may store one or more identifiers (e.g., a filename, a number, a filename extension, etc.) that correspond to the types of video content identified in content type field 615. Taxonomy field 620 may, in one example, store information associated with a filename convention for different types of video content. The filename convention may, for example, identify respective different filenames, and/or other identifiers, associated with different types of video assets (e.g., video assets with different resolutions, bit rates, frame refresh rates, etc.), different types of metadata (e.g., text, cover art images, descriptions of video assets, etc.), different types of information associated with DRM (e.g., a key, a license, etc.).

Metadata transform policy field 625 may store information associated with a format that corresponds to metadata, which may be used, by ingestion server 310, to identify a manner in which the metadata is to be converted to another format (e.g., a standard format that can be processed by ingestion server 310 and/or VCM system 240). Decryption policy field 630 may store information that identifies a manner in which the video content, obtained from the particular content provider 130, is to be decrypted. In one example, decryption policy field 630 may store a key that ingestion server 130 may use to decrypt the video content.

Figure 7:
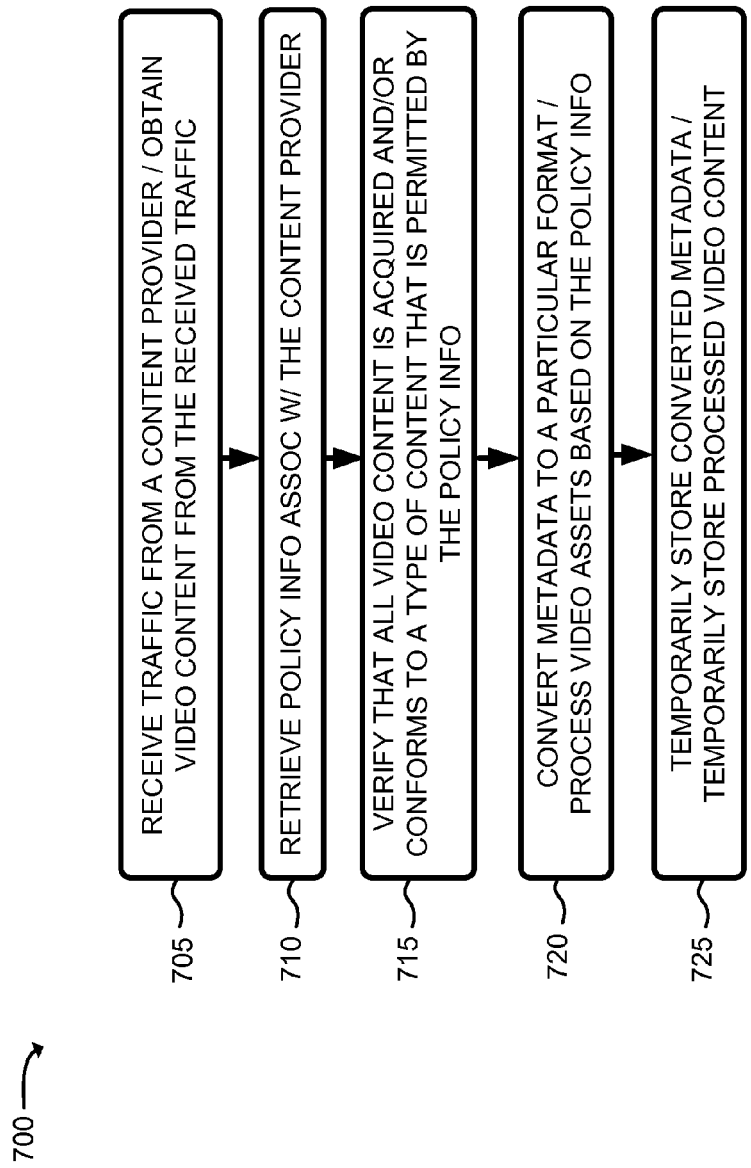
FIG. 7 is a flow chart of an example process for acquiring video content from a content provider, within a video content management system.

FIG. 7 is a flow chart of an example process 700 for acquiring video content from a content provider 130. In one example implementation, process 700 may be performed by one or more devices associated with ingestion server 310. In another example implementation, some or all of process 700 may be performed by a device, or collection of devices separate from, or in combination with ingestion server 310.

As shown in FIG. 7, process 700 may include receiving traffic from a content provider and obtaining video content from the received traffic (block 705). For example, acquisition module 505, hosted by ingest server 310, may communicate with content provider 130, via network 150, to acquire the video content (e.g., using a file transfer protocol (FTP) and/or some other protocol) and may communicate with NAS module 515 to temporarily store the acquired video content in an ingest memory associated with VCM system 240. In another example, ingestion server 310 may monitor a memory associated with VCM system 240, that is accessible by content provider 130, to determine whether content provider 130 has downloaded video content to the memory. Ingestion server 130 may detect the video content, within the memory, and may cause a copy of the video content to be stored in the ingest memory. In yet another example, ingestion server 310 may acquire video content by reading video content from a portable storage device (e.g., a video tape, a DVD, etc.), and may cause the video content, read from the portable storage device, to be temporarily stored in the ingest memory. In still another example, ingestion server 310 may acquire video content via a media stream received from content provider 130 and may cause the video content to be temporarily stored in the ingest memory.

Ingestion server 310 may also acquire video content from content provider 130 via a remote server device (e.g., a web server), associated with network 150, and may cause the video content to be temporarily stored in the ingest memory. In a further example, ingestion server 310 may acquire metadata, associated with video assets that are included within the video content and may temporarily store the metadata in a metadata repository associated with VCM system 240.

As also shown in FIG. 7, process 700 may include retrieving policy information associated with the content provider (block 710) and verifying that all of the video content is acquired and/or conforms to a type of content permitted by the policy information (block 715). For example, acquisition module 505 may retrieve, from a memory associated with ingestion server 310, policy information associated with content provider 130 as described above with respective to data structure 600 of FIG. 6. Acquisition module 505 may verify whether all of the video content, such as all files associated with a video asset, metadata, and/or information associated with DRM, have been received from content provider 130. For example, acquisition module 505 may compare identifiers associated with the video content (e.g., filenames, numbers, file name extensions, etc. associated with video assets, metadata, information associated with DRM, etc.) to identifiers that are permitted to be included in the video content as identified in the policy information (e.g., via taxonomy field 620 of FIG. 6). If the identifiers, obtained from the video content, do not match identifiers that are included in the policy information, acquisition module 505 may send a notification to content provider 130 requesting that the video content be retransmitted. In another example, acquisition module 505 may send a notification to workflow module 510 indicating that the video content is to be retransmitted and workflow module 510 may communicate with content provider 130 to cause the video content to be retransmitted. If, however, the identifiers, obtained from the video content, match identifiers that are included in the policy information, acquisition module 505 may communicate with NAS module 515 (e.g., directly and/or via workflow module 510) to temporarily store the video content for further processing.

In another example, acquisition module 505 may compare types of the video content (e.g., types of video assets, of metadata, of information associated with DRM, etc.) to types of video content that are permitted to be included in the video content as identified in the policy information (e.g., via content type field 615 of FIG. 6). If the types of the video content do not match the types of video content that are included in the policy information, acquisition module 505 may, in a manner similar to that described above, cause content provider 130 to retransmit the video content. If, however, the types of the video content match the types of video content that are permitted in the policy information, acquisition module 505 may cause the video content to be temporarily stored, in the ingest memory, for further processing.

Acquisition module 505 may send a notification to workflow module 510, hosted by VCMS controller 350, indicating that the video content has been received, from content provider 130, and/or the content of the video content is complete and/or conforms to a particular format based on the policy information. Workflow module 510 may receive the notification and may transmit an instruction, to acquisition module 505 to acquire the video content by decrypting and/or decompressing the video content received from content provider 130.

As further shown in FIG. 7, process 700 may include converting the metadata to a particular format and/or processing video assets based on the policy information (block 720). For example, ingestion server 310 by use acquisition module 505 and/or metadata module 535, to convert the metadata, obtained from the video content, to a particular format that can be processed by VCM system 240 and/or VPS 120. The particular format may identify a respective format associated with text (e.g., formats for descriptions of video assets, etc.), images (e.g., formats for cover art associated with video assets), and/or data (e.g., formats for ratings, symbols, icons, etc.) that may be included in the metadata. The conversion may be performed based on the policy information. For example, acquisition module 505 and/or metadata module 535 may obtain, from the policy information, information associated with a manner in which the metadata is to be converted from the format, in which the metadata was transported, to the particular format (e.g., based on information identified in metadata transform policy field 625 of FIG. 6). Additionally, or alternatively, acquisition module 505 and/or metadata module 535 may decompress the metadata based on the policy information.

Acquisition module 505 may send a notification, to workflow module 510, indicating that the metadata has been converted to the particular format and/or decompressed. Workflow module 510 may receive the notification and may send an instruction to store the metadata, as acquired metadata, in a metadata repository associated with VCM system 240. In another example implementation, the metadata may be converted and/or decompressed by metadata processor 330 (e.g., using metadata module 535) in a manner similar to that described above.

Ingestion server 310 may decrypt and/or decompress video assets, obtained from the video content, based on the policy information. Ingestion server 310 may use acquisition module 505 and/or decryption module 520 to obtain information associated with a decryption policy, from the policy information, and may use the information associated with the decryption policy to decrypt and/or decompress the video assets. Acquisition module 505 may send a notification, to workflow module 510, indicating that the video assets have been decrypted and/or decompressed based on the policy information. Workflow module 510 may receive the notification and may send an instruction to store the video assets, as acquired video assets, in the ingest memory associated with VCM system 240. In another example implementation, the video assets may be decrypted and/or decompressed by content processor 320 (e.g., using decryption module 520) in a manner similar to that described above.

As yet further shown in FIG. 7, process 700 may include temporarily storing the converted metadata and/or the processed video content (block 725). For example, ingestion server 310 may receive an instruction, from VCMS controller 350 (e.g., via workflow module 510) to temporarily store the acquired video assets in the ingest memory. Acquisition module 505 may, in response to the instruction, temporarily store the decrypted and/or decompressed video assets in the ingest memory. In one example, NAS module 515 may erase and/or overwrite (e.g., with the acquired video assets) the video content that was temporarily stored in the ingest memory when received from content provider 130.

In another example, ingestion server 310 may receive an instruction, from VCMS controller 350 (e.g., via workflow module 510) to temporarily store the acquired metadata in the ingest memory and/or metadata repository. Acquisition module 505 may, in response to the instruction, cause the acquired metadata to be temporarily stored in the ingest memory and/or the metadata repository. In one example, NAS module 515 may erase and/or over-write (e.g., with the acquired metadata) the metadata that was temporarily stored in the metadata repository when received from content provider 130.

Ingestion server 310 may send (e.g., via acquisition module 510) a notification to VCMS controller 350 (e.g., to workflow module 510) indicating that the acquired video content and/or acquired metadata has been temporarily stored in the ingest memory and/or metadata repository.

Figure 8:
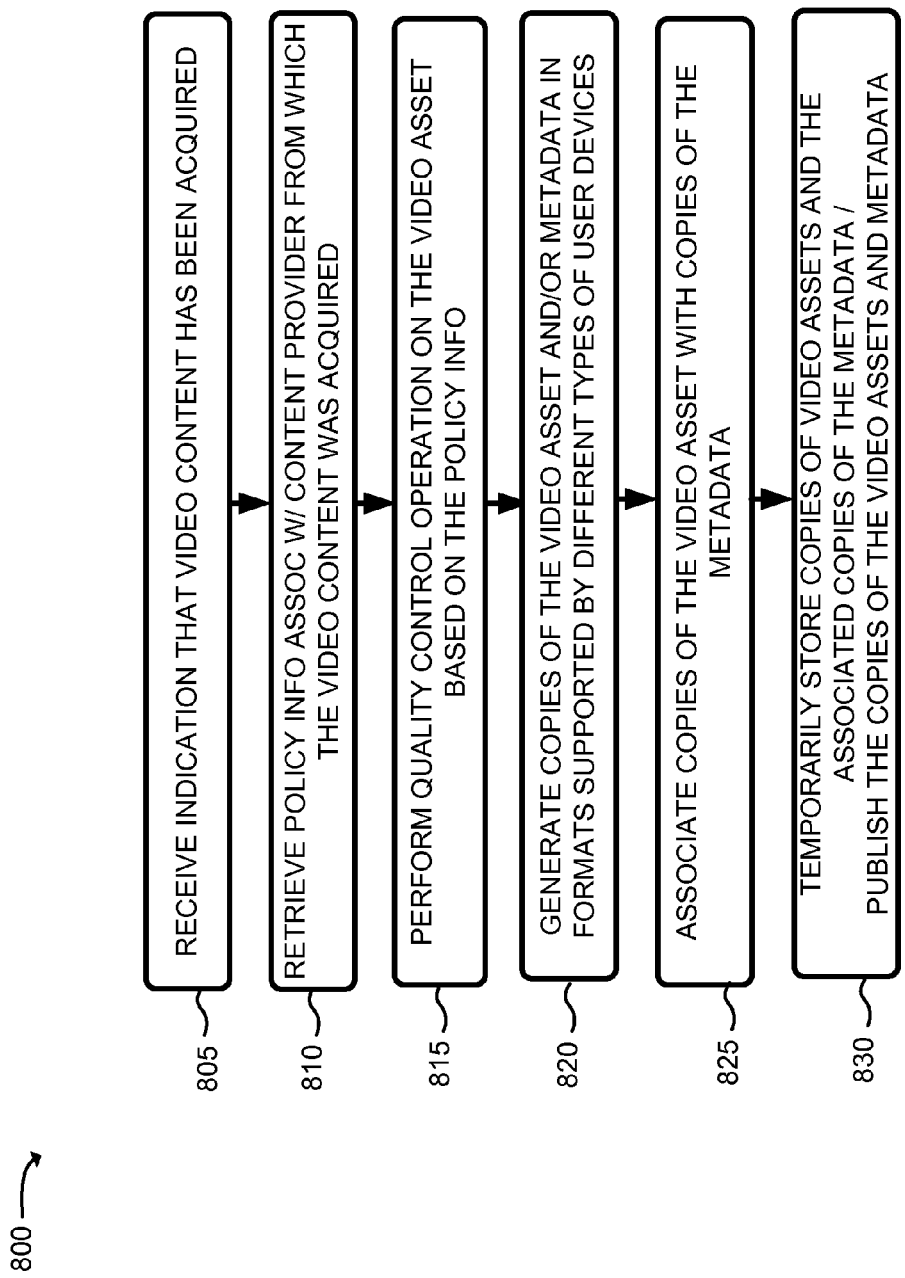
FIG. 8 is a flow chart of an example process for processing acquired video content that enables the video provisioning system to provide a video provisioning service to different types of user devices.

FIG. 8 is a flow chart of an example process 800 for processing acquired video content that enables VPS 120 to provide a video provisioning service to different types of user devices. In one example implementation, process 800 may be performed by one or more devices associated with VCM system 240. In another example implementation, some or all of process 800 may be performed by a system and/or device, or collection of systems and/or devices separate from, or in combination with the devices associated with VCM system 240.

As shown in FIG. 8, process 800 may include receiving an indication that video content has been acquired (block 805) and retrieving policy information associated with a content provider from which the content was acquired (block 810). For example VCMS controller 350, may receive a notification from ingest server 310, that video content has been acquired from content provider 130. The notification may indicate that a video asset, associated with the acquired video content, has been stored in an ingest memory. Additionally, or alternatively, the notification may indicate that metadata has been stored in a metadata repository and/or another memory (e.g., the ingest memory).

Workflow module 510, hosted by VCMS controller 350, may retrieve policy information, associated with content provider 130, as a result of receiving the indication that the video content has been acquired. The policy information may be retrieved from a data structure (e.g., data structure 600 of FIG. 6) that is stored in a memory associated with VCM system 240. In another example implementation, workflow module 510 may, as a result of the receiving the indication that the video content has been acquired, send an instruction to content processor 320 and/or metadata processor 330 to retrieve the policy information.

As also shown in FIG. 8, process 800 may include performing a quality control operation on the video asset based on the policy information (block 815). For example, workflow module 510 may cause VCM controller 350 to send an instruction to quality module 525, hosted by content processor 320, to perform a quality control operation on the video asset. Quality module 525 may receive the instruction and quality module 520 may perform the quality control operation on the video asset based on the policy information.

Quality module 525 may, for example, examine the video asset (e.g., video signals, audio signals, etc.), to identify a condition associated with the video asset. Quality module 525 may play and/or analyze the video asset to identify a condition associated with video and/or audio that corresponds to the video asset. The condition may render a blank and/or distorted display, and/or a silent and/or distorted sound, respectively, when played on user device 110. The condition may be identified, by quality module 525, when the blank and/or distorted display, and/or the silent and/or distorted sound occur for a period of time that is greater than a threshold. Quality module 525 may perform an operation to reduce the period of time, associated with the blank and/or distorted display, and/or the silent and/or distorted sound, to a duration that is less than the threshold.

Quality module 525 may also examine the video asset to verify that the video asset complies with video and/or audio standards (e.g., MPEG-2, MPEG-4, H.264, VC-1, etc.), video and/or audio formats (e.g., QCIF, CIF, SD, HD, etc.), and/or specifications that are utilized by VPS 120 and/or specified by an operator associated with VPS 120. Quality module 525 may repair the video asset to enable the video asset to conform to the video and/or audio standards, video and/or audio formats, and/or the specification. If, however, quality module 525 is not able to repair the video asset, and/or to reduce the period of time to the duration that is less than the threshold, quality module 525 may send a notification, to workflow module 510, indicating that condition cannot be repaired. Workflow module 510 may communicate with content provider 130 to reacquire the video content.

As further shown in FIG. 8, process 800 may include generating copies of the video asset and/or metadata in formats that are supported by different types of user devices 110 (block 820) and associating the copies of the video assets with the copies of the metadata (block 825). For example, workflow module 510 may send an instruction to transcode module 530 to generate copies of the video asset and/or to convert each copy, of the video asset, to a respective format that can be supported (e.g., received, processed, stored, played, etc.) by different types of user devices 110 (e.g., a set top box, a computer device, a wireless handset device, a gaming device, etc.). For example, transcode module 530 may generate one or more copies of the video asset.

Transcode module 530 may transcode each copy of the video asset in a manner that can be supported by respective different types of user device 110. One copy of the video asset may, for example, by transcoded to conform to a bit rate, a level of resolution (e.g., standard definition, high definition, etc.), a frame refresh rate, a screen size (e.g., aspect ratios, dimensions, etc.) that can be supported by a wireless handset user device 110. Another copy of the video asset may be transcoded to conform to another bit rate, level of resolution, frame refresh rate, screen size, etc. that can be supported by a set top box user device 110. Further copies of the video asset may be transcoded to conform to further bit rates, levels of resolution, frame refresh rates, screen sizes, etc. that can be supported by a computer user device 110, a gaming user device 110, and/or another type of user device 110.

Workflow module 510 may send an instruction to metadata module 535 to generate copies of the metadata in a respective format that can be supported (e.g., received, processed, stored, displayed, etc.) by different types of user devices 110. The respective formats may include image formats, text formats (e.g., fonts, spacing, etc.), descriptions (e.g., descriptions and/or summaries of video assets that conform to parameters such as screen space, word count, etc.) that are formatted to be displayed on the different types of user devices 110.

Workflow module 510 may associate the copies of the metadata with the copies of the video assets based on each of the different types of user device 110. For example, workflow module 510 may identify a copy of the metadata, that corresponds to a type of user device 110 (e.g., a computer device), and may logically associate the copy of the metadata to a copy of the video asset that has been transcoded to be supported by the type of user device 110. Workflow module 510 may associate other copies of the metadata, that correspond to other types of user device 110 (e.g., a set top box, a gaming device, a wireless handset device, etc.), with other copies of the video assets in a similar manner.

As yet further shown in FIG. 8, process 800 may include temporarily storing the copies of the video asset and/or the associated copies of the metadata and/or publishing the copies of the video assets and/or the metadata (block 830). For example, transcode module 530 may store the transcoded copies of the video asset in a publish memory, associated with VCM system 240, that may allow a publication operation to be performed on the transcoded copies of the video assets. Additionally, or alternatively, metadata module 535 may store the copies of the metadata in a metadata repository and/or the publish memory, associated with VCM system 240. Transcode module 530 and/or metadata module 535 may send respective notifications to workflow module 510 that indicates that the copies of the video assets and/or the metadata, respectively, have been temporarily stored and/or are ready for publication.

Workflow module 510 may receive the respective notifications and may, in response to the respective notifications, instruct publication module 540, hosted by publication server 340, to initiate a publication operation. Publication module 540 may, in response to the instruction, retrieve the copies of the video assets from the publish memory and may transmit the copies of the video assets to VOD server 225 and/or CDN server 230. Publication module 540 may, in another example, retrieve the copies of the metadata from the publish memory and/or the metadata repository and may transmit the copies of the metadata to content catalog 235 and/or VOD server 225. VOD server 225 may receive copies of the metadata and may cause the copies of the metadata, associated with the set top box user device 110, to be published to a store front (e.g., an IMG), hosted by IMG server 220. The store front may be accessed by set top box user device 110 in order to obtain a copy of the video asset from VOD server 225.

Catalog server 235 may receive the copies of the metadata and may cause the copies of the metadata, associated with types of user device 110 other than a set top box-type of user device 110, to be published to another store front (e.g., a user interface, a webpage, a interactive program guide (IPG), etc.), hosted by application server 215. The other store front may be accessed by a computer device a wireless handset device, a gaming device, etc. to obtain a respective copy of the video asset from CDN server 230.

Systems and/or methods, described herein, may enable video content to be acquired, from a content provider, by a video content management system (VCMS). The systems and/or methods may enable the VCMS to acquire the video content by decrypting the video content and/or verifying that all of the video content has been received and/or conforms to a particular format. The systems and/or methods may enable the VCMS to process the acquired video content that enables the acquired video content to be ingested into a video provisioning system with which the VCMS is associated. The systems and/or methods may enable the VCMS to process the acquired video content by verifying that the acquired video content complies with video and/or audio standards and/or conforms to a particular level of quality. The systems and/or methods may also enable the acquired video content to be processed and/or published so that different types of user devices can access, obtain, and/or play the video content.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with regard to FIGS. 7 and 8, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
  receiving, by one or more devices, video content from one or more content providers;
  processing, by the one or more devices, the video content based on one or more policies, where processing the video content includes:
    examining the video content to determine whether a gap is associated with the video content, where the gap renders a blank screen for a period of time that is greater than a threshold when the video content is played by a user device,
    determining whether the period of time, associated with the gap, can be reduced to another period of time that is not greater than the threshold,
    communicating with the one or more content providers to obtain another copy of the video content based on a determination that the period of time cannot be reduced to the other period of time, and
    repairing the video content by causing the period of time to be reduced to the other period of time based on a determination that the period of time can be reduced to the other period time;
  generating, by the one or more devices and as a result of processing the video content, copies of the video content, where each of the copies of the video content conform to a respective different format that is supported by a set top box and another device, the other device being a different type of device than the set top box; and
  storing, by the one or more devices, the copies of the video content.

2. The method of claim 1, further comprising:
  retrieving policy information, associated with the one or more content providers, where the policy information includes:
    a list of files to be included in the video content, or
    a list of one or more types of files that are permitted to be included in the video content;
  determining that all of the video content has been received when the video content includes each of the files identified in the list of files; and
  determining that the video content can be acquired, by the one or more devices, when each of the files, included in the video content, conforms to a respective type of file that is identified in the list of one or more types of files that are permitted to be included in the video content.

3. The method of claim 1, where receiving the video content from the one or more content providers includes at least one of:
  receiving a video stream, from the one or more content providers, that includes the video content;
  communicating with a server device, that hosts a website via which the video content is obtained;
  obtaining the video content from a portable storage device; or
  communicating with the one or more content providers to obtain the video content.

4. The method of claim 1, where the video content includes a video asset and at least one of:
  metadata, where the metadata enables the video asset to be managed or offered to the set top box or the other device by the one or more devices, or
  information associated with data rights management (DRM), where the information associated with the DRM includes a license that enables the video asset to be decrypted or played by the set top box or the other device.

5. The method of claim 1, where processing the video content further includes:
   evaluating the video content to determine whether the video content conforms to a video standard;
   retrieving another copy of the video content, from the one or more content providers, based on a determination that the video content does not conform to the video standard; and
   ingesting the video content based on a determination that the video content conforms to the video standard, where ingesting the video content allows the video content to be formatted in a manner that can be played on the set top box or the other device.

6. The method of claim 1, where generating the copies of the video content further include:
   identifying a first format, associated with a video asset included in the video content, that can be received, processed, or played on the set top box;
   identifying a second format, associated with the video asset, that can be received processed, or played by the other device;
   generating a first copy of the video content based on the first format; and
   generating a second copy of the video content based on the second format.

7. The method of claim 6, where the first format includes at least one of:
   a first bit rate that can be supported by the set top box,
   a first frame refresh rate that can be supported by the set top box, or
   a first level of resolution that can be supported by the set top box; and
   where the second format includes at least one of:
   a second bit rate that can be supported by the other device,
   a second frame refresh rate that can be supported by the other device, or
   a second level of resolution that can be supported by the other device.

8. The method of claim 1, where generating the copies of the video content further include:
   generating a first copy of metadata, associated with a video content, obtained from the video content, where the first copy of the metadata includes one or more images associated with the video content or a text-based description of the video content, that are formatted to be displayed on the set top box;
   generating a second copy of the metadata, where the second copy of the metadata includes the one or more images associated with the video content or the text-based description of the video content, that are formatted to be displayed on the other device.

9. The method of claim 1, where the other user device includes at least one of:
   a computer device,
   a tablet computer,
   a wireless handset device, or
   a gaming device.

10. A system comprising:
    one or more processors to:
    receive video content from a content provider,
    retrieve policy information associated with the content provider,
    determine that the video content conforms to one or more formats permitted by the policy information,
    process the video content based on the determination that the video content conforms to the one or more formats, where processing the video content includes:
       performing a quality control operation on the video content to verify that a condition is not associated with the video content, wherein the condition is identifiable by silence or a distorted sound that occurs for a period of time that is greater than a threshold,
    determine that a condition is associated with other video content, received from the content provider, based on a quality control operation performed on the other video content, where the condition corresponds to distorted video or a blank screen when played by a set top box or an other device, and where the distorted video or the blank screen exists for a period of time that is greater than a second threshold,
    perform an operation to remedy the condition based on a determination that the condition can be remedied, where remedy in the condition causes the distorted video or the blank screen to exist for another period of time that is not greater than the second threshold,
    retrieve another copy of the other video content based on a determination that the condition cannot be remedied,
    generate one or more copies of the processed video content, where a first copy, of the one or more copies, is supported by the set top box and a second copy, of the one or more copies, is supported by the other device, the other device being a different type of device than the set top box, and
    store the one or more copies of the processed video content.

11. The system of claim 10, where the one or more processors are further to:
    execute a first module, of one or more modules, that controls a logical workflow associated with one or more operations performed on the video content, where other modules, of the one or more modules, include at least one of:
    a second module to receive the video content,
    a third module to decrypt or decompress the video content,
    a fourth module to perform the quality control operation on the video content, or
    a fifth module to transcode the copies of the video asset.

12. The system of claim 11, where the one or more modules act as a service oriented architecture (SOA) that permits the first module to call all or a portion of the other modules, based on the logical workflow, to perform any of the one or more operation on the video content.

13. The system of claim 10, where the policy information includes at least one of:
    a list of files that the content provider indicates are to be included in the video content,
    a list of types of video content that the content provider indicates are to be included in the video content,
    information associated with a manner in which the video content is to be decrypted, or
    information that identifies a manner in which metadata, associated with the video content, is to be converted to a particular format.

14. The system of claim 10, where the one or more processors are further to:
    generate one or more copies of metadata, associated with the video content, where the one or more copies of the metadata, are formatted for the set top box and the other device, and where the metadata is obtained from the video content.

15. A system, comprising:
    one or more devices to:

receive a video asset from one or more content providers;

process the video asset to allow the video asset to be provided to a set top box and another device, the other device being a different type of device than the set top box, where processing the video asset includes:
verifying that the video asset conforms to one or more predetermined formats,
decrypting the video asset,
verifying that the video asset complies with a particular standard of quality,
transcoding the video asset in a manner that is supported by the set top box and the other device,
examining the video asset to determine whether a gap is associated with the video asset, wherein the gap renders a blank screen for a period of time that is greater than a threshold when the video asset is played by a user device,
determining whether the period of time, associated with the gap, can be reduced to another period of time that is not greater than the threshold, and
repairing the video asset by causing the period of time to be reduced to the other period of time based on a determination that the period of time can be reduced to the other period time, and store the transcoded video asset.

16. The system of claim 15, where, when receiving the video asset, the one or more devices are further to:
receive a video stream, from the one or more content providers, that includes the video asset;
retrieve the video asset from another device, associated with the one or more content providers;
obtain the video asset from a portable storage device; or
communicate with the one or more content providers to obtain the video asset.

17. The system of claim 15, where the one or more devices are further to:
retrieve policy information associated with the one or more content providers, where the policy information includes at least one of:
information that identifies constituent parts of the video asset that the one or more content providers indicate is a complete video asset,
information that identifies the one or more predetermined formats to which the constituent parts of the video asset are to conform,
information that identifies a manner by which to decrypt the video asset, or
information that identifies a manner by which metadata, associated with the video asset, is to be converted to a particular format.

18. The system of claim 17, where, when processing the video asset, the one or more devices are further to:
compare one or more formats, associated with the constituent parts of the video asset, with the one or more predetermined formats obtained from the policy information,
verify that the video asset conforms to the one or more predetermined formats when the one or more formats matches the one or more predetermined formats, and
retrieve, from the one or more content providers, another copy of the video asset when at least one of one or more formats does not match any of the one or more predetermined formats.

19. The system of claim 17, where, when processing the video asset, the one or more devices are further to:
convert the metadata to the particular format, based on the information that identifies the manner by which metadata is to be converted to the particular format.

20. The system of claim 15, where, when processing the video asset, the one or more devices are further to:
transcode the video asset to create a first copy of the video asset that can be played by the set top box, where the first copy corresponds to at least one of:
a first bit rate associated, a first level of resolution,
a first frame refresh rate, or
a first compression/decompression (CODEC) ratio, and
transcode the video asset to create one or more copies of the video asset that can be played by the other device, where the one or more copies of the video asset correspond to at least one of:
a second bit rate,
a second level of resolution, or
a second frame refresh rate associated with the video asset.

21. The system of claim 15, further comprising:
one or more storage devices to store the video asset at various stages of processing, where the one or more storages devices include:
a first storage device to temporarily store the video asset when the video asset is received from the one or more content providers;
a second storage device to permanently store the video asset, as a source video asset, when the video asset is verified to conform with the standard of quality, where the source video asset is used to generate copies of the video asset for transcoding, and
a third storage device to temporarily store the generated copies of the video asset that have been transcoded and from which the generate copies of the video asset are provided to the video provisioning system for distribution to the set top box or the other device.

* * * * *